US005968983A

United States Patent [19]
Kaesemeyer

[11] Patent Number: 5,968,983
[45] Date of Patent: Oct. 19, 1999

[54] METHOD AND FORMULATION FOR TREATING VASCULAR DISEASE

[75] Inventor: Wayne H. Kaesemeyer, Augusta, Ga.

[73] Assignee: Nitrosystems, Inc, Augusta, Ga.

[21] Appl. No.: 08/833,842

[22] Filed: Apr. 10, 1997

Related U.S. Application Data

[63] Continuation-in-part of application No. 08/693,882, Aug. 5, 1996, Pat. No. 5,767,160, which is a continuation-in-part of application No. 08/321,051, Oct. 5, 1994, Pat. No. 5,543,430.

[51] Int. Cl.⁶ .................................................. A01N 37/12
[52] U.S. Cl. .......................... 514/564; 514/565; 514/460
[58] Field of Search .................................. 514/565, 460, 514/564

[56] References Cited

U.S. PATENT DOCUMENTS

| | | | |
|---|---|---|---|
| 4,686,211 | 8/1987 | Hara et al. | 514/148 |
| 5,059,712 | 10/1991 | Griffith | 562/560 |
| 5,132,453 | 7/1992 | Griffith | 562/560 |
| 5,158,883 | 10/1992 | Griffith | 435/240.2 |
| 5,196,195 | 3/1993 | Griffith | 424/94.6 |
| 5,273,875 | 12/1993 | Griffith | 435/1 |
| 5,316,765 | 5/1994 | Folkers et al. | 424/94.1 |
| 5,366,738 | 11/1994 | Rork et al. | 424/473 |
| 5,428,070 | 6/1995 | Cooke et al. | 514/557 |
| 5,543,430 | 8/1996 | Kaesemeyer | 514/565 |

OTHER PUBLICATIONS

Morris et al., "An integrated approach to the selection of optimal salt from a new drug candidate", International Journal of Pharmaceutics (Amsterdam), 105(3), 209–217, 1994, see abstract.

Patel, J. M. et al. Nitric Oxide Exposure and Sulfhydryl Modulation Alter L–Arginine Transport in Cultured Pulmonary Artery Endothelial Cells. (Abstract Only) Free Radical Biology & Medicine. vol. 20, No. 5. p. 629. 1996.

Xia, Y. et al. Nitric Oxide Synthase Generates Superoxide and Nitric Oxide in Arginine–Depleted Cells Leading to Peroxynitrite–Mediated Cellular Injury. Proc. Natl. Acad. Sci. USA. vol. 93. pp. 6770–6774. Jun. 1996.

Jeremy, R. W. et al. Effects of Dietary L–Arginine on Atherosclerosis and Endothelium–Dependent Vasolidation in the Hypercholesteralemic Rabbit. Circulation. Vol. 94, No. 3. pp. 498–506. Aug. 1, 1996.

Block, E. R. et al. Hypoxia Inhibits L–Arginine Uptake By Pulmonary Artery Endothelial Cells. (Abstract Only) Am. J. Physiol. vol. 269. L574–L580. 1995.

Mayer, B. et al. Brain Nitric Oxide Synthase is a Biopterin–and Flavin–Containing Multi–Functional Oxido–Reductase. (Abstract Only) FEBS 10045. vol. 288, No. 1,2. pp. 187–191. Aug. 1991.

Weidinger, F. F. et al. Persistent Dysfunction of Regenerated Endothelium After Balloon Angioplasty of Rabbit lliac Artery. Circulation. vol. 81, No. 5. pp. 1667–1679. May 1990.

Chester, A. H. et al. Low Basal and Stimulated Release of Nitric Oxide in Atherosclerotic Epicardial Coronary Arteries. The Lancet. vol. 336. pp. 897–900. Oct. 13, 1990.

Albina, J. E. et al. Arginine Metabolism in Wounds. Am. J. Physiol. vol. 254. pp. E459–E467. 1988.

Cooke, J.P. et al. Antiatherogenic Effects of L–Arginine in the Hypercholesterolemic Rabbit. (Abstract Only) J. Clin. Invest. vol. 90, No. 3. pp. 1168–1172. Sep. 1992.

Nakamura, Y. et al. Pravastatin Reduces Restenosis After Coronary Angioplasty of High Grade Stenotic Lesions: Results of SHIPS (SHIga Pravastatin Study). (Abstract Only). Cardiovasc. Drugs. Ther., vol. 10, No. 4, pp. 475–483. 1996.

Pohl, U. et al. Effects of LDL on Intracellular Free Calcium and Nitric Oxide–Dependent cGMP Formation on Porcine Endothelial Cells. (Abstract only) Atherosclerosis. vol. 117. pp. 169–178. 1995.

Deliconstantinos, G. et al. Modulation of Particulate Nitric Oxide Synthase Activity and Peroxynitrate Synthesis in Cholesterol Enriched Endothelial Cell Membranes. (Abstract Only) Biochem. Pharm. vol. 49. No. 11. pp. 1589–1600. 1995.

Galle, J. et al. Effect of HDL and Atherogenic Lipoproteins on Formation of O2 and Renin Release in Juxtaglomerular Cells. (Abstract Only) Kidney International. vol. 51. pp. 253–260. 1997.

Bult, H. Nitric Oxide and Atherosclerosis: Possible Implications for Therapy. (Abstract only) Molecular Medicine Today. p. 510. Dec. 1996.

Crouse III, J.R. et al. Pravastatin, Lipids, and Atherosclerosis in the Carotid Arteries (PLAC–II). (Abstract only) Am. J. Cardiol. vol. 75. pp. 455–459. 1995.

Aji, W. et al. L–Arginine Prevents Xanthoma Development and Inhibits Atherosclerosis in LDL Receptor Knockout Mice. (Abstract only) Circulation. vol. 95. pp. 430–437. 1997.

Cooke, J. P. et al. Arginine: A new Therapy for Atherosclerosis?. Circulation. vol. 95. pp. 311–312. 1997.

Boger, R. H. et al. The L–Arginine Nitric Oxide Pathway: Role in Atherosclerosis and Therapeutic Implications. (First page only) Atherosclerosis. vol. 127. pp. 1–11. 1996.

Jay, M.T. et al. Modulation of Vascular Tone By Low Density Lipoproteins. Effects on L–Arginine Transport and Nitric Oxide Synthesis. Experimental Physiology. vol. 82. pp. 349–360. 1997.

Muramatsu, J. et al. Hemodynamic Changes Associated with Reduction in Total Cholesterol By Treatment with the HMG–CoA Reductase Inhibitor Pravastatin. Atherosclerosis. vol. 130. pp. 179–182. 1997.

(List continued on next page.)

*Primary Examiner*—Dwayne C. Jones
*Attorney, Agent, or Firm*—Reed Smith Shaw McClay LLP; Raymond A. Miller

[57] ABSTRACT

A therapeutic mixture comprised of L-arginine and inhibitors of Hmg—CoA-Reductase is disclosed for the treatment of diseases related to endothelial dysfunction, wherein the endothelial dysfunction is relieved by stimulating the constitutive form of nitric oxide synthase (cNOS) to produce native nitric oxide (NO).

19 Claims, 2 Drawing Sheets

OTHER PUBLICATIONS

Sacks, F. M. et al. The Effect of Pravastatin on Coronary Events After Myocardial Infarction in Patients with Average Cholesterol Levels. The New England Journal of Medicine. vol. 335. pp. 1001–1009. Oct. 3, 1996.

Bovan, A. J. van. et al. Reduction of Transient Myocardial Ischemia with Pravastatin in Addition to the Conventional Treatment in Patients with Angina Pectoris. Circulation. vol. 94. pp. 1503–1505. 1996.

Lacoste, L. et al. Comparative Effect of Pravastatin and Simvastatin on Platelet–Thrombus Formation in Hypercholesterolemic Coronary Patients. JACC. vol. 27 No. 2 Supp A. p. 413A. 1996.

Pitt, B. et al. Pravastatin Limitation of Atherosclerosis in the Coronary Arteries (PLAC I): Reduction in Atherosclerosis Progression and Clinical Events. J. Am. Coll. Cardiol. vol. 26. pp. 1133–1139. 1995.

Candipan, R.C. et al. Regression or Progression: Dependency on Vascular Nitric Oxide. Arterioscler. Thromb. Vas. Biol. vol. 16. pp. 44–50. 1996.

Byington, R.P. et al. Reduction in Cardiovascular Events During Pravastatin Therapy. Pooled Analysis of Clinical Events of the Pravastatin Atherosclerosis Intervention Program. Circulation. vol. 92. pp. 2419–2425. 1995.

Pritchard, K.A. et al. Native Low–Density Lipoprotein Increases Endothelial Cell Nitric Oxide Synthase Generation of Superoxide Anion. Circ. Res. vol. 77 No. 3. pp. 510–518. 1995.

Boger, R.H. et al. Supplementation of Hypercholesterolemic Rabbits with L–Arginine Reduces the Vascular Release of Superoxide Anions and Restores NO Production. Artherosclerosis. vol. 117 No. 2. pp. 273–284. 1995.

Lacoste, L. et al. Correction of the Increased Thrombogenic Potential with Cholesterol Reduction. Circulation. vol. 92. pp. 3172–3177. 1995.

Shepard, J. Prevention of Coronary Heart Disease with Provastatin in Men with Hypercholesterolemia. The New England Journal of Medicine vol. 333. pp. 1301–1307. Nov. 16, 1995.

Philis–Tsimikas, A. et al. L–Arginine May Inhibit Atherosclerosis Through Inhibition of LDL Oxidation. Circulation. vol. 92 (Supp. I). pp. I–422. 1995.

Von der Leyen, H.E. et al. Gene Therapy Inhibiting Neointimal Vascular Lesion: In Vivo Transfer of Endothelial Cell Nitric Oxide Synthase Gene. Proc. Natl. Acad. Sci. USA. vol. 92. pp. 1137–1141. 1995.

Egashira, K. et al. Reduction in Serum Cholesterol with Pravastatin Improves Endothelium–Dependent Coronary Vasomotion in Patients with Hypercholesterolemia. Circulation. vol. 89. pp. 2519–2524. 1994.

Tsao, P. et al. Enhanced Endothelial Adhesiveness in Hypercholesterolemia is Attenuated by L–Arginine. Circulation. vol. 89. pp. 2176–2182. 1994.

Cayatte, A.J. et al. Chronic Inhibition of Nitric Oxide Production Accelerates Neointima Formation and Impairs Endothelial Function in Hypercholesterolemic Rabbits. Arterioscler. Thomb. vol. 14. pp. 753–759. 1994.

Wilcox, J.N. et al. Expression of Multiple Nitric Oxide Synthase Isoforms in Human Aortic Fatty Streaks and Advanced Atherosclerotic Plaques. (Abstract only) Circulation. vol. 90 (Supp. I). pp. I–298. 1994.

Chen, L. Y. et al. Oxidated LDL Decreases L–Arginine Uptake and Nitric Oxide Synthase Protein Expression in Human Platelets: Relevance of the Effect of Oxidized LDL on Platelet Function. Circulation. vol. 93. pp. 1740–1746. 1993.

Wada, H. et al. Hypercoagulable State in Patients with Hypercholesterolemia: Effects of Pravastatin. Clin. Therap. vol. 14. pp. 829–834. 1992.

Dresler, H. et al. Correction of Endotelial Dysfunction in Coronary Microcirculation of Hypercholesterolaemia Patients by L–Arginine. The Lancet. vol. 338. pp. 1546–1550. Dec. 21/28, 1991.

Haman, M. et al. Long–Term Oral Administration of L–Arginine Reduces Intimal Thickening and Enhances Neoendothelium–Dependent Acetylcholine–Induced Relaxation After Arterial Injury. Circulation, vol. 90. No. 3, pp. 1357–1362. Sep., 1994.

Harrison, D.G. Endothelial Modulation of Vascular Tone: Relevance to Coronary Angioplasty and Restenosis. J. Am. Coll. Cardiol. vol. 17. pp. 71B–76B. 1991.

Cooke, J.P. et al. Arginine Restores Cholinergic Relaxation of Hypercholesterolemic Rabbit Thoracic Aorta. Circulation. vol. 83. pp. 1057–1062. 1991.

Witzum, J.L. et al. Role of Oxidized Low Density Lipoprotein in Atherogenesis. J. Clin. Invest. vol. 88. pp. 1785–1792. 1991.

Mugge, A.J. et al. Chronic Treatment with Polyethylene–Glycolated Superoxide Dismutase Partially Restores Endothelium–Dependent Vascular Relaxations in Cholesterol–Fed Rabbits. Circ. Res. vol. 69. pp. 1293–1300. 1991.

Forstermann, U. et al. Selective Attenuation of Endothelium–Mediated Vasodilation in Atherosclerotic Human Coronary Arteries. Circ. Res. vol. 62. pp. 185–191. 1988.

Cohen, R.A. et al. Loss of Selective Endothelial Cell Vasoactive Functions in Pig Coronary Arteries During Hypercholesterolemia. Circ. Res. vol. 63. pp. 903–910. 1988.

Schwarzacher, A.P. et al. Locak Intramural Delivery of L–Arginine Enhances Nitric Oxide Generation and Inhibit Lesion Formation After Balloon Angioplasty. Circulation, vol. 95. No. 7. pp. 1863–1869. Apr. 1, 1997.

Verbeuren, T.J. et al. Effect of Hypercholesterolemia on Vascular Reactivity in the Rabbit., I: Endothelium–Dependent and Independent Contractions and Relaxations in Isolated Arteries of Control and Hypercholesterolemic Rabbits. Circ. Res. vol. 58. pp. 552–564. 1986.

Duggan, D.E. et al. The Physiological Disposition of Lovastatin. Drug Metabolism and Disposition, vol. 17, No. 2. pp. 166–173. 1989.

Vickers, S. et al. Metabolic Disposition Studies on Simvastatin, a Cholesterol–Lowering Prodrug. Drug Metabolism and Disposition, vol. 18, No. 2. pp. 138–145. 1990.

Cooke, J. P. et al., "Antiatherogenic Effects of L–Arginine in the Hypercholesterolemic Rabbit.", Abstract only, J. Clin. Invest. vol. 90, No. 3, pp. 1168–1172, Sep. 1992.

Pitt, B. et al., Pravastatin Limitation of Atherosclerosis in the Coronary Arteries (PLAC I): Reduction in Atherosclerosis Progression and Clinical Events. J. Am. Coll. Cardiol. vol. 26. pp. 1133–1139, 1995.

METHOD AND FORMULATION FOR TREATING VASCULAR DISEASE

This application is a continuation-in-part application of application Ser. No. 08/693,882 filed Aug. 5, 1996, issued as U.S. Pat. No. 5,767,160 on Jun. 16, 1998, which is a continuation-in-part application of application Ser. No. 08/321,051 filed Oct. 5, 1994, issued as U.S. Pat. No. 5,543,430 on Aug. 6, 1996.

BACKGROUND OF THE INVENTION

This invention relates generally to a method of treating cardiocerebrorenovascular disease as well as avoiding potential cardiocerebrorenovascular disease, and the symptoms thereof, wherein a substrate of Nitric Oxide Synthase ("NOS") and an agonist of NOS are combined to produce a beneficial effect.

DESCRIPTION OF RELATED ART

Much focus in the area of cardiac disease has been on the presence of cholesterol in the body. Hypercholesterolemia is known to be a primary risk factor for death from coronary heart disease. It is known that 50% or more of the total body cholesterol in humans is derived from intrinsic biosynthesis. It is also known that a rate-limiting step of major significance in the biosynthesis of cholesterol is at the level of the enzyme known as 3-hydroxy-3-methylglutaryl-coenzyme A reductase or Hmg—CoA reductase. A general class of compounds is known in the art which inhibit and reduce the intrinsic biosynthesis of cholesterol in order to reduce the risk factor of hypercholesterolemia and coronary artery death. This general class of compounds is known as inhibitors of Hmg—CoA reductase.

An alternative approach to treating cardiac disease is to effect the dilation of vascular conduits in the body. In this regard, nitric oxide has been shown to be formed enzymatically as a normal metabolite from arginine in vascular endothelium and provides an important component to the formation of endothelium-derived relaxing factor (EDRF). EDRF appears to be equivalent to Endothelium Derived Nitric Oxide (EDNO) and as used herein EDRF and EDNO are interchangeable unless otherwise indicated. Macrophages and neurons have also been shown to produce nitric oxide in the body as a component of their cell killing and/or cytosolic function.

Recently it has been established that a family of enzymes called Nitric Oxide Synthase ("NOS") form nitric oxide from L-arginine, and the nitric oxide produced is responsible for the endothelium dependent relaxation and activation of soluble guanylate cyclase, nuerotransmission in the central and peripheral nervous systems, and activated macrophage cytotoxicity.

Nitric Oxide Synthase, occurs in many distinct isoforms which include a constitutive form (cNOS) and an inducible form (iNOS). The constitutive form is present in normal endothelial cells, neurons and some other tissues. Formation of nitric oxide by the constitutive form in endothelial cells is thought to play an important role in normal blood pressure regulation, prevention of endothelial dysfunction such as hyperlipodemia, arteriosclerosis, thrombosis, and restenosis. The inducible form of nitric oxide synthase has been found to be present in activated macrophages and is induced in vascular smooth muscle cells, for example, by various cytokines and/or microbial products.

The conversion of precursor substrates of EDNO such as L-arginine into nitric oxide is enzymatically catalyzed by NOS and the resulting by-product of the conversion of L-arginine is L-citrulline. Although it was initially described in endothelium, NOS activity has now been described in many cell types. Brain, endothelium, and macrophage isoforms appear to be products of a variety of genes that have approximately 50% amino acid identity. NOS in brain and in endothelium have very similar properties, the major differences being that brain NOS is cytosolic and the endothelial enzyme is mainly a membrane-associated protein.

Functionally, the constitutive form of Nitric Oxide Synthase ("cNOS"), which is the predominant synthase present in brain and endothelium, may be active under basal conditions and can be further stimulated by increases in intracellular calcium that occur in response to receptor-mediated agonists or calcium ionophores. cNOS appears to be the "physiological" form of the enzyme and plays a role in a diverse group of biologic processes. In vitro studies suggest that the activity of nitric oxide synthase can be regulated in a negative feedback manner by nitric oxide itself. In cardiocerebrorenovascular circulation, the primary target for constitutively produced nitric oxide is believed to be soluble guanylate cyclase located in vascular smooth muscle, the myocardium (myocytes) and coronary vascular smooth muscle.

In contrast to the cNOS, the inducible, calcium-independent form, iNOS was initially only described in macrophages. It is now known that induction of nitric oxide synthase can occur in response to appropriate stimuli in many other cell types. This includes both cells that normally do not express a constitutive form of nitric oxide synthase, such as vascular smooth muscle cells, as well as cells such as those of the myocardium that express considerable levels of the constitutive isoform.

iNOS exhibits negligible activity under basal conditions, but in response to factors such as lipopolysaccharide and certain cytokines, expression occurs over a period of hours. The induced form of the enzyme produces much greater amounts of NO than the constitutive form, and induced NOS appears to be the "pathophysiological" form of the enzyme because high concentrations of NO produced by iNOS can be toxic to cells. Induction of iNOS can be inhibited-by glucocorticoids and some cytokines. Relatively little is known about postranscriptional regulation of iNOS. Cytotoxic effects of NO are probably largely independent of guanylate cyclase and cyclic GMP formation. Most of the research in the area has focused on inhibitors of iNOS stimulation using various derivatives of L-arginine.

Research into the area of cNOS activation reveals a number of agonist of cNOS some of which have been described in U.S. Pat. No. 5,543,430, which is hereby incorporated by reference in its entirety. However, until now there was no known research indicating Hmg—CoA reductase inhibitors were capable of functioning as agonist of cNOS.

SUMMARY OF THE INVENTION

The term "subject" as used herein to mean any mammal, including humans, where nitric oxide formation from arginine occurs. The methods herein for use on subjects contemplate prophylactic use as well as curative use in therapy of an existing condition.

The term "native NO" as used herein refers to nitric oxide that is produced through the bio-transformation of L-arginine or the L-arginine dependent pathway. "EDRF" or "EDNO" may be used interchangeably with "native NO". The term endpoints as used herein refers to clinical events encountered in the course of treating cardiovascular disease, up to and including death (mortality)

L-arginine as used herein includes all biochemical equivalents (i.e. salts, precursors, and its basic form). L-arginine as defined herein appears to function as a substrate of cNOS.

"To mix", "mixing", or "mixture(s)" as used herein means mixing a substrate (i.e. L-arginine) and an agonist (i.e. Hmg—CoA reductase inhibitor): 1) prior to administration ("in vitro mixing"); 2) mixing by simultaneous and/or consecutive, but separate (i.e. separate intravenous lines) administration of substrate (L-arginine and agonist to cause "in vivo mixing"; and 3) the administration of a NOS agonist after saturation with a NOS substrate (i.e. L-arginine is administered to build up a supply in the body prior to administering the NOS agonist (nitroglycerin or Hmg—CoA reductase)); or any combination of the above which results in the combination of therapeutic amounts of a NOS agonist and a NOS substrate in an additive or synergistic way with regard to the treatment of vascular disease.

Agonist refers to an agent which stimulates the bio-transformation of a substrate such as L-arginine to EDNO or EDRF either through enzymatic activation or increasing gene expression (i.e. increased protein levels of c-NOS). Of course, either or both of these mechanisms may be acting simultaneously.

It is an object of this invention to provide a method of preventing, treating, arresting, or ameliorating disease conditions which are benefited by the bio-transformation of a substrate into endogenous nitric oxide or "native" nitric oxide.

It is another object of this invention to provide a method of preventing, treating, arresting, or ameliorating disease conditions which are benefited by the bio-transformation of L-arginine into "native" nitric oxide through enzyme activation of NOS.

It is another object of this invention to ameliorate or avoid tachycardia and prevent or treat ischemia.

It is another object of this invention to achieve a beneficial effect when treating disease conditions by increasing or maximizing the production of "native" nitric oxide, and reducing clinical endpoints to include mortality.

It is another object of this invention to prevent reperfusion injury in subjects who have had abrupt restoration of blood flow.

It is a further object of this invention to provide a mixture of inhibitors of Hmg—CoA reductase and biological equivalents of L-arginine for the treatment of hypertension, hypertensive heart disease, coronary heart disease, including arteriosclerosis, angina, myocardial infarction, coronary thrombosis, restenosis post angioplasty, and sudden death, as well as a wide range of cardiovascular disease (heart failure, stroke, and peripheral vascular diseases), and renovascular ischemia/hypertension.

These and other objects of this invention are provided by one or more of the embodiments provided below.

In one embodiment of the invention, therapeutically effective amounts of a precursor of EDNO and an agonist of NOS are combined prior to administration to a patient. In another embodiment of the invention, therapeutically effective amounts of a precursor of EDNO and an agonist of NOS are combined prior to administered separately and mixed "in vivo".

In another embodiment of the invention, therapeutically effective amounts of L-arginine and inhibitors of Hmg—CoA reductase are mixed at a physiologically acceptable pH and administered to a patient.

In another embodiment of the invention a method for treating hypertension in a subject by vasodilation or vasorelaxation comprises: selecting a hypertensive subject; administering L-arginine and Hmg—CoA reductase inhibitors to the subject; obtaining periodic blood pressure measurements of the subject; and continuing administration of L-arginine and Hmg—CoA reductase inhibitors until a desirable blood pressure or therapeutic effect is detected in the subject. A desirable blood pressure in a hypertensive subject should ultimately be within the following ranges: systolic preferably in the range of 95–180 mmHg, more preferably in the range of 105–165 mmHg, and even more preferably in the range of 120 to 140 mmHg; and 15 diastolic preferably in the range of 55–115 mmHg, more preferably in the range of 65–100 mmHg, and even more preferably in the range of 70 to 90 mmHg, and most preferably 75–85 mmHg. Under no circumstances should the systolic be permitted to go below 95 mmHg.

Another embodiment of the present invention is a method for preventing or treating cardiovascular disease in a non-hypertensive subject by vasodilation or vasorelaxation comprising: selecting a subject; administering to said subject a formulation comprising a mixture of an inhibitor of Hmg—CoA reductase and an endothelium dependent source of nitric oxide (i.e., L-arginine); obtaining periodic measurements of vasorelaxation on the subject and; continuing administration of the formulation until a desirable state of vasorelaxation or desirable therapeutic effect is detected on the subject. A desirable state-of vasorelaxation is for example a lowering of the systolic by about 20 mmHg and a lowering of the diastolic by about 10 mmHg. Under no circumstances should the systolic be lowered less than 95 mmHg.

Yet another embodiment is a method for stimulating cNOS in a subject which comprises: selecting a subject; administering to said subject a formulation comprising a mixture of L-arginine and inhibitors of Hmg—CoA reductase, so as to maximize "native" NO production and reduce endpoints to include mortality.

DETAILED DESCRIPTION OF THE PREFERRED EMBODIMENTS

Figure 1:
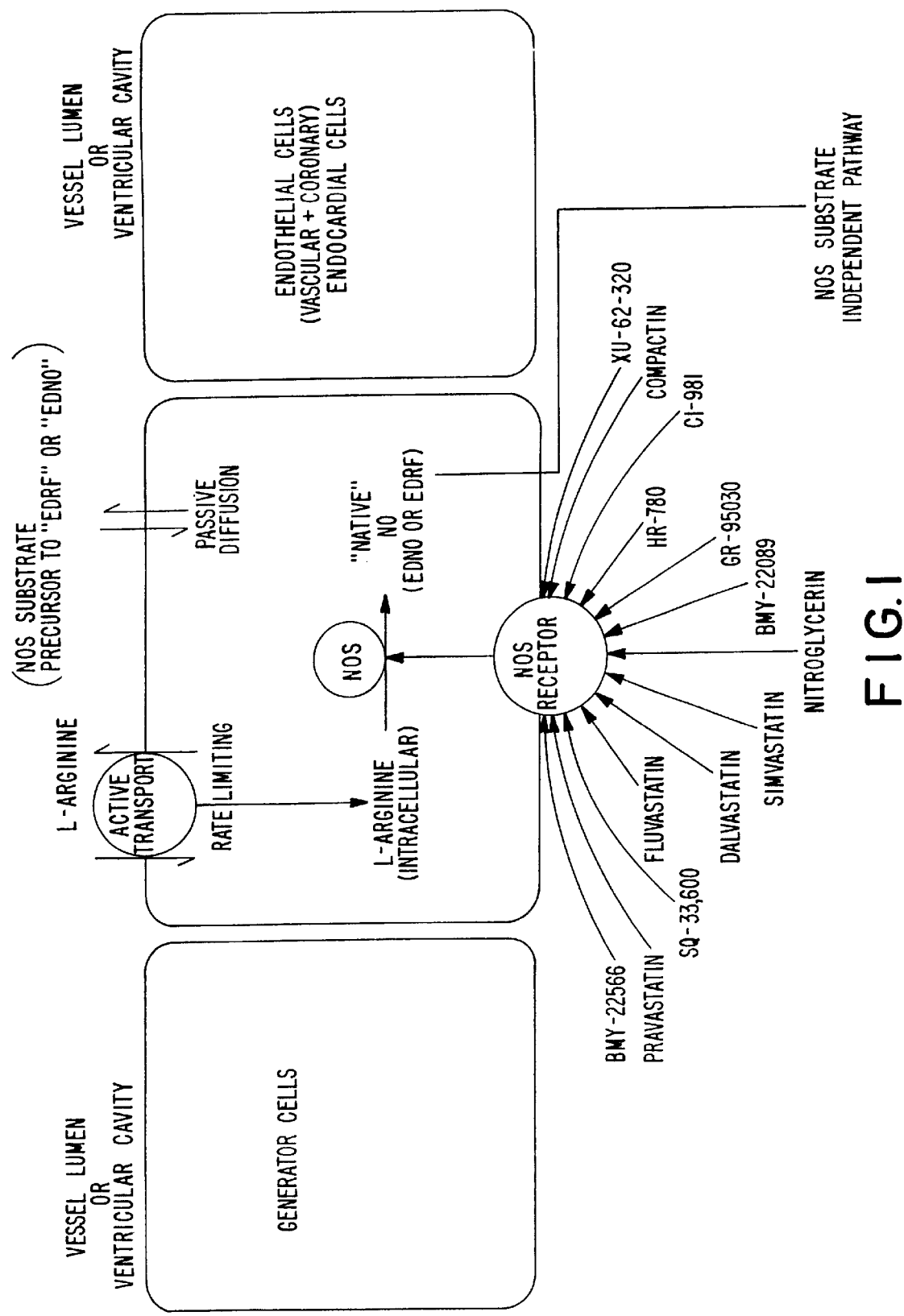
FIG. 1 is a schematic representation of the proposed NOS activation pathway.

From the data presented herein it appears that inhibitors of Hmg—CoA reductase may have dual applicability in the treatment of hypertension and cardiovascular diseases such that they act as both an inhibitor of the intrinsic biosynthesis of cholesterol and a stimulator or agonist of nitric oxide synthase. The fact that Hmg—CoA reductase may be agonist or stimulant of nitric oxide synthase has remarkable implications. Mixing inhibitors of Hmg—CoA reductase "in vitro" or "in vivo" with L-arginine has been found to have an unforeseen beneficial effect that is most likely due to excess L-arginine providing additional substrate for the nitric oxide synthase and the NOS being catalyzed to enzymatically increase the bio-transformation of L-arginine into nitric oxide.

Stimulation of NOS in the presence of excess L-argintine or other substrate precursor of native NO (EDRF or EDNO) may be used to prevent, treat, arrest, or ameliorate any disease or condition which is positively affected by NO production. Such conditions include hypertensive cardiocerebrorenovascular diseases and their symptoms as well as non-hypertensive cardiocerebrorenovascular diseases. The mixture is particularly useful for subjects in need of native NO production. Application of such a mixture is beneficial for: (1) Chronic stable angina; (2) Unstable angina; (3) Acute myocardial infarction; (4) Hibernating myocardium; (5) Stunned myocardium; (6) Limitation of ventricular remodeling in post myocardial infarction and subsequent risk of congestive heart failure; (7) Prophylaxis of recurrent myocardial infarction; (8) Prevention of sudden death following myocardial infarction; (9) Vasospastic angina; (10) Congestive heart failure-systolic-seen in association with 1–6 above; (11) Congestive heart failure-diastolic-seen in association with 1–10 above and 12–15 below; (12) Microvascular angina seen in association with 1–11 above and 15 and 16 below; (13) Silent ischemia seen in association with 1–12 above and 15 and 16 below; (14) Reduction of ventricular ectopic activity seen in association with 1–13 above and 15 below; (15) Any or all of the above 1–14 states of ischemic myocardium associated with hypertensive heart disease and impaired coronary vasodilator reserve; (16) control of blood pressure in the treatment of hypertensive crisis, perioperative hypertension, uncomplicated essential hypertension and secondary hypertension; (17) Regression of left ventricular hypertrophy seen in association with 15 and 16 above; (18) Prevention and or regression of epicardial coronary arteriosclerosis seen in 1–17 above; (19) Prevention of restenosis post angioplasty; (20) Prevention and/or amelioration of free radical mediated reperfusion injury in association with 1–19 above; (21) Use of the combination in the prevention of myocardial injury during cardioplegic arrest during coronary bypass or other open heart surgery i.e. use of the combination as a cardioplegic solution; (22) Post transplant cardiomyopathy; (23) Renovascular ischemia; (24) Cerebrovascular ischemia (TIA) and stroke); and (25) Pulmonary hypertension.

Vascular smooth muscle cells are located mainly in veins, arteries, and coronary arteries. The following discussion focuses on smooth muscle and myocyte relaxation stimulated by vasodilators. As discussed above the nitric oxide synthase in the cells is normally cNOS, the constitutive form of nitric oxide synthase, and the generator cells are endothelial cells and the target cells are vascular smooth muscle cells. FIG. 1 is a schematic illustration and is not intended to imply any cellular relationship or geography of the various sites of action, but rather meant to illustrate their functional relationship.

The principle combination to be employed will be a mixture that involves therapeutic concentrations of L-arginine and a Hmg—CoA reductase inhibitor in water. Any pharmaceutical grade L-arginine will be sufficient and should be diluted preferably to 2.5–60% w/v (g/ml), more preferably to 5–45% w/v (g/ml), even more preferably between 7.5–30% w/v (g/ml), even more preferably to 10–15% w/v (g/ml), and most preferably 10% w/v (g/ml) L-arginine. The typical doses anticipated will be 30 grams of L-arginine in sterile water (Total Volume 300 cc). L-arginine is anticipated eventually to be approximately 10:1 to about 25:1 of the hydrochloride salt to L-arginine as a base, and even more preferably 15:1 to about 20:1 hydrochloride salt to base, and most preferably 15:1 hydrochloride salt to base. In this example 28 to 29 grams will be the hydrochloride salt and 1 to 2 grams of L-arginine will be base.

L-arginine may be used in conjunction with virtually any of the family of those substances known as Hmg—CoA reductase inhibitors. Those particular Hmg—CoA reductase inhibitors most preferred for use in conjunction with the present formulation as selected from the group consisting of: simvastatin, lovastatin, pravastatin, compactin, fluvastatin, dalvastatin, HR-780, GR-95030, CI-981, BMY 22089, and BMY 22566. U.S. Pat. No. 5,316,765 cites a number of these Hmg—CoA reductase inhibitors and is hereby incorporated by reference in its entirety. In particularly preferred embodiments of the present invention, the Hmg—CoA reductase inhibitor utilized is pravastatin or lovastatin. In an even more particularly preferred embodiments, the administration of the present invention includes the Hmg—CoA reductase inhibitor pravastatin.

As part of a "mixture", the Hmg—CoA reductase inhibitor is included together with L-arginine and clinically effective weight ratios of between 1:2 to 1:150. Even more particularly, the ratio of the Hmg—CoA reductase L-arginine in the formulation is between 1:5 to 1:100. The most preferred embodiment of the "mixture" the ratio of Hmg—CoA reductase inhibitor, most particularly pravastatin, to L-arginine is 1:50. The range of ratios of an Hmg—CoA reductase inhibitor to L-arginine may be employed with virtually any Hmg—CoA reductase inhibitor.

Where the particular Hmg—CoA reductase inhibitor is pravastatin, the ratio of pravastatin to L-arginine is preferably within the range 1:2 to 1:50, Wt/Wt. For example, pravastatin/L-arginine at a ratio of 1:2 would include 40 mg/day pravastatin with 80 mg/day L-arginine. Where the ratio of pravastatin/L-arginine is at a ratio of 1:20, for example, 20 mg/day pravastatin would be administered with 400 mg/day L-arginine. Weight ratio of ingredients described herein in regard to the Hmg—CoA reductase inhibitors, lovastatin and pravastatin are applicable for any Hmg—CoA reductase inhibitor. The amounts above have been found to be effective, however, each route of administration (i.e. IV, oral, transdermal, etc.) will vary in their requirements.

Even more particularly, the presently disclosed "mixtures" may be described in terms of their relative concentrations (grams) administered as part of a continuous daily and/or monthly regimen. In one particular embodiment, the formulation is administered so as to provide the patient with between 20–40 milligrams per day of the Hmg—CoA reductase inhibitor (i.e., pravastatin) together with a daily dose of L-arginine of between 100 to 200 mg per day. Most preferably, the Hmg—CoA reductase inhibitor, such as lovastatin, is administered at a daily dose of about 20 mg per day together with a dose of about 200 mg per day L-arginine. This particular embodiment of the claimed formulation should maintain within the patient efficient levels of the formulation.

By way of example only, Table 1 presents a listing of several inhibitors of Hmg—CoA reductase. These substances vary in their potency and their abilities to inhibit Hmg—CoA.

TABLE 1

Simvastatin
Lovastatin
Pravastatin
Compactin (a.k.a., mevastatin)
Fluvastatin
Dalvastatin
GR-95030
HR-780
SQ 33,600
BMY 22089

TABLE 1-continued

BMY 22566
CI981

The Hmg—CoA reductase inhibitors of the present invention are also characterized by an ability to stimulate receptor-mediated clearance of hepatic low-density lipoproteins (LDL), as an anti-hypercholesterolemic, and as a competitive inhibitor of Hmg—CoA reductase.

The Hmg—CoA reductase inhibitor employed may be lovastatin, simvastatin, pravastatin, XU-62-320 (Sodium 3.5-dihydroxy-7 [3-(4-fluorophenyl)-1(methylethyl)-IH-Indole-2yl]-hept-6-enoate), mevastatin (a.k.a., compacting, BNY 22089, CI-981, SQ 33,600, BMY 22089, CI 981, HR 780, SQ 33,600 or any other member of the class of compounds that inhibit Hmg—CoA reductase. The preparation of lovastatin, simvastatin, and pravastatin have been described in the patent literature. The preparation of XU-62-320 (fluvastatin) is described in WIPO Patent W084/02131. BMY 22089(13), CI 981(14), HR 780(15), and SQ 33,600 (16) are also described in the literature cited, and are specifically incorporated herein by reference for the purpose of even more fully describing the chemical structure and synthesis of these Hmg—CoA reductase inhibitors. These methods of preparation are hereby incorporated by reference in their entirety.

Also within the scope of those Hmg—CoA reductase inhibitors of the present invention are included the bioactive metabolites of those compounds listed in Table 1, such as pravastatin sodium (the bio-active metabolite of mevastatin).

Any one or several of those Hmg—CoA reductase inhibitor compounds listed in Table 1 pravastatin may be mixed with L-arginine or substrate precursor to endogenous nitric oxide to provide a therapeutically effective treatment for a patient.

Until now there was no link between the biotransformation of L-arginine into "native" nitric oxide and anti-hypocholesterolemic Hmg—CoA reductase inhibitors. However, it is now believed that Hmg—CoA reductase inhibitors has a stimulating effect on cNOS. The mechanism is not well understood but it appears the mixture of inhibitors of Hmg—CoA reductase and L-arginine may have a heretofore unexpected synergistic effect on cNOS stimulation. The stimulation of cNOS may be a result of cNOS having a unique receptor site for Hmg reductase inhibitors or inhibitors of Hmg—CoA reductase initiating a cascade of events which stimulate NO. Administering the two also provides adequate substrate for cNOS processing of L-arginine since the L-arginine is added in excess while at the same time stimulation the enzymatic activity of NOS. Whether it is a synergistic effect or additive effect, what is clear is that "mixing" a precursor substrate of "native" nitric oxide with a Hmg—CoA reductase inhibitor results in a heretofore unexpected increase in NO production. This unexpected affect is demonstrated in the example below.

EXAMPLE

The direct effects of acteylcholine and pravastatin on NO production in bovine aortic endothelial cells (BAEC) was determined using a highly sensitive photometric assay for conversion of oxyhemoglobin to methemoglobin. NO oxidize; oxyhemoglobin ($HbO_2$) to methemoglobin (metHb) in the following reaction $HbO_2+NO\rightarrow metHb+NO_3$. The amount of NO produced by endothelial cells was quantified by measuring the change in absorbance as $HbO_2$ oxidizes to metHb. Oxyhemoglobin has a absorbance peak at 415 nm, while metHb has a 406 nm absorbance peak. By subtracting the absorbance of metHb from $HbO_2$, the concentration of NO can be assessed. The general method was patterned after that of Feelisch et aL, (Biochem. and Biophy. Res. Comm. 1991; 180, Nc I:286–293).

For this assay, endothelial cells were isolated from bovine aortas. BAECs were grown to confluency in 150 mm plates (Coming) using Medium 199 supplemented with penicillin G (100 $mL^{-1}$), streptomycin (100 $mL^{-1}$), glutamine (100 $mL^{-1}$), thymidine (100 $mL^{-1}$), and 10% fetal calf serum (Gibco). Upon confluency, cells will be washed twice with a 1% phosphate buffered saline/EDTA solution. Tripsin/EDTA was added and the cells were kept at 37° C. until the cells become rounded thus signaling detachment from the plate. An equal amount of trypsin inhibitor was added to inhibit any further trypsin activity that might damage the cells. The cells were pelleted by spinning at 150–200 g for 5 min. Cells were resuspended in culture medium and approximately $10^7$ of these cells were used to inoculate 0.5 g of micro-carrier beads (Cytodex #3). Cells, beads and medium was transferred to a spinner flask (Wheaton) where the culture sat undisturbed at 37° C. with 95% $O_2$ and 5% $CO_2$ for 29 min then spun (20 rpm) in this same environment for 1 min. This sitting cycle allowed for cell adherence to the beads while the spinning created an even distribution of cells and beads. After 4 hrs of this attachment phase, the spinner flask was left on the stirrer at slow speed for 2–3 days for uniform cellular coating of beads.

Beads/cells were rinsed twice and then suspended in a Hepes-buffered Krebs-Ringer solution containing all necessary co-factors. To prevent a reaction between NO and superoxide ($O_2$), superoxide dismutase (200 U/ml) was added to the buffer. Catalase (100 U/ml) will be added to decompose hydrogen peroxidase, keeping the hemoglobin active. Two ml of EC/beads were placed into a water-jacketed chromatography column (Pharmacia) and superfused at 2 ml/min with Hepes-buffered Krebs-Ringers solution containing 3 uM oxyhernoglobin. The perfusate was then directed into a flow-through cuvettte in a dual wavelength spectrophotometer and absorbance was measured to determine the basal and stimulated NO release. A parallel column circuit was filled with only beads (no cells) to determine basal and spontaneous release of NO in this system without cells. Vehicle (buffer w/o agent) did not cause a change in absorbance when infused into the cell-bead column.

Experimental stimulation were carried out by 3 min infusion periods of acetylcholine (ACH) or pravastatin (PRA) added to buffer perfusion using a micro syringe pump at a rate of 45 ul/min to yield a final concentration of $10^{-6}$ and $10^{-5}$ M for ACH and $10^{-6}$ and $10^{-5}$ M for PRA in the buffer. The effects of buffer containing L-NAME ($10^{-3}$ M) in blocking the actions of these drug agents and then a buffer without L-NAME but with excess L-arginine ($10^{-3}$ M) in reversing any L-NAME effect was examined. Each drug agent concentration was given twice for each of the three buffer systems; a period of 10 min was allowed between infusion of agents. Our data demonstrate that this cell perfusion and monitoring system remains stable for at least 4–6 hours. At the end of each experiment, cell viability was checked using trypan blue exclusion.

For analysis, we determined the area under the curve for the change in absorbance response/unit time (min) caused by each agent above baseline levels and calculated metHb production using an extinction coefficient of 39 mM[1]. During the 3 min infusion of agents, absorbance increases rapidly. Changes in absorbance to these agents usually persist from 2–8 mins depending on the size of the response before returning to baseline levels. We assume a one to one correspondence for NO and metHb production, the known stoichiometric balance for this reaction. We also determined changes in basal NO production during perfusion with each of the buffer systems. Basal NO values were subtracted from any drug-induced responses to determine NO production which results from the drug's actions. Table 2 recites the results of these experiments.

TABLE 2

| | Basic Buffer | $10^{-3}$M L-NAME | $10^{-3}$M L-arginine |
|---|---|---|---|
| | (absolute production of NO in nmole* min) | | |
| $10^{-6}$M Ach | 197.60 | 72.20 | 330.60 |
| $10^{-5}$M Ach | 619.40 | 288.80 | 756.20 |
| $10^{-6}$M Prav. | 163.40 | 45.60 | 201.40 |
| $10^{-5}$M Prav. | 513.00 | 209.00 | 752.40 |

Figure 2:
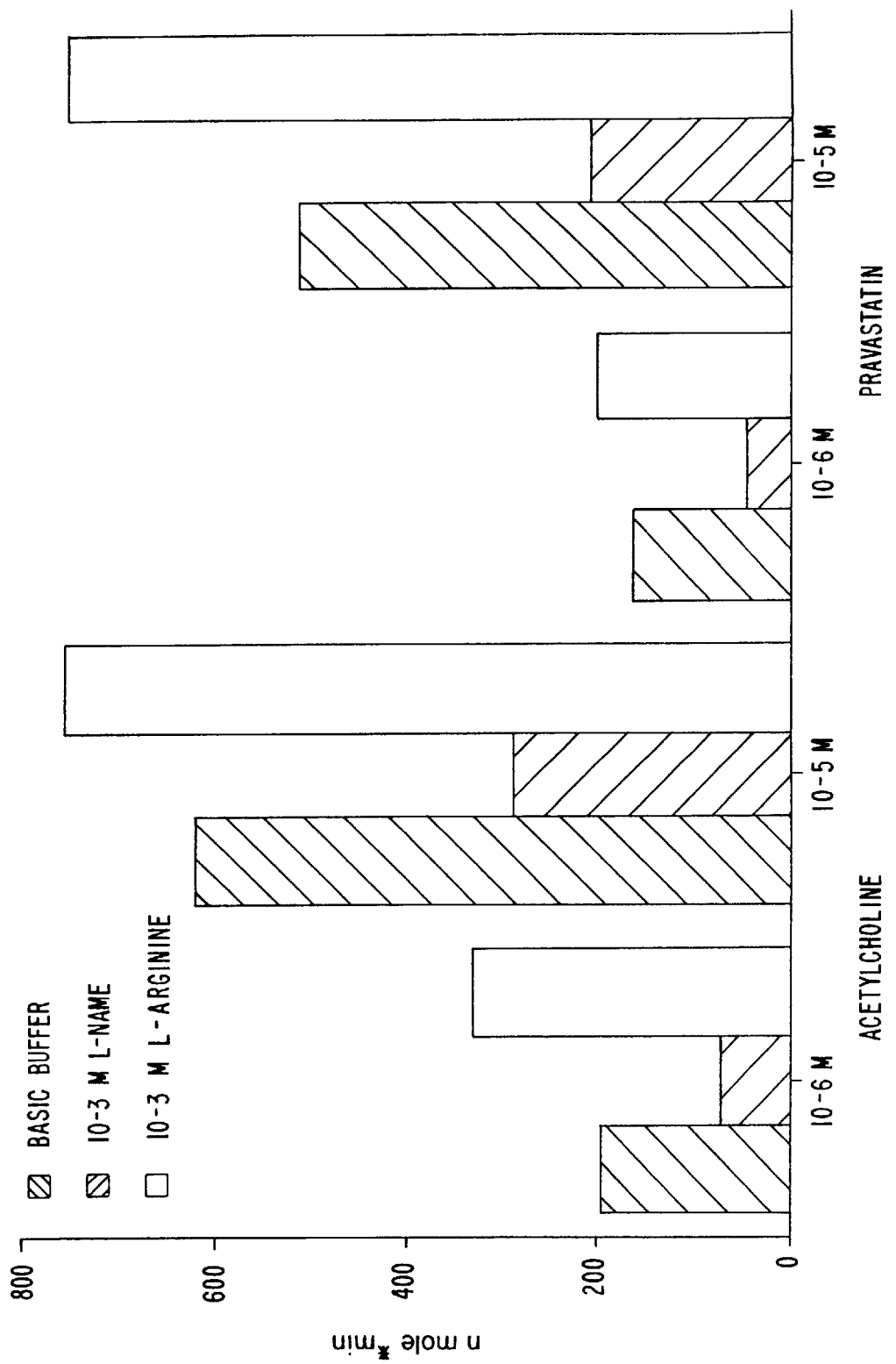
FIG. 2 is a bar graph illustrating the stimulation of NOS with pravastatin.

FIG. 2 is a bar graph of the data generated which illustrates the effects of acetylcholine and pravastatin ($10^{-6}$ and $10^{-5}$ M) administered for 3 min periods into the cell/bead perfusion system on NO production with: 1) $10^{-5}$ M L-arginine in control (basic) buffer, 2) $10^{-3}$ M of L-NAME in buffer, and 3) $10^{-3}$ M of L-arginine in buffer. Responses are transient elevations in NO production above basal levels. Data for responses in L-NAME and L-arginine augmented buffer are presented as percent of response in control buffer (100%); numbers in basic buffer bars indicate absolute production of NO in nmole *min. The remaining two bars denote differences between responses in L-NAME buffer vs both basic and L-arginine added buffers.

The effects of pravastatin on activity of endothelial cells in producing NO were compared with those of acetetylcholine, which is known to specifically stimulate NO production by NOS activity. Adding acetylcholine to the buffer superfusion bovine aortic endothelial cells (BAECs) grown on beads increased their production of NO as measured by oxidation of oxyhemoglobin to methemoglobin (FIG. 2) Acetylcholine produced a transient, concentration-related increase in NO above baseline levels. In basic buffer containing 5×$10^{-5}$ M L-arginine, and there was approximately a two fold increase in NO production between $10^{-5}$ M L-arginine, there was approximately a two fold increase in NO production between $10^{-5}$ and $10^{-6}$ M acetylcholine. Subsequent treatment of these cells with buffer containing L-NAME, $10^{-3}$ M markedly reduced acetylcholine-induced production of NO by 80%. When this L-NAME buffer was replaced with another containing increased L-arginine ($10^{-3}$ M), acetylcholine-elicited production of NO returned to control levels.

Pravastatin also caused a concentration-related increase in NO production above baseline levels. There was a larger increment in response to the $10^{-5}$ M concentrations of pravastatin (~3 X) compared with that of acetylcholine. Superfusion of the cell suspension with L-NAME ($10^{-3}$ M), also blunted NO production in response to pravastatin. This suggests that NO production is due at least in part to NOS activity. Subsequent perfusion of the cells with a buffer containing L-arginine $10^{-3}$ M resulted in a return in NO production to a level above the amount induced by the Pravastatin in control (basis) buffer. This restoration of response to Pravastatin after L-arginine addition was greater than that observed for acetylcholine. Administration of Pravastatin or acetylcholine into a perfusion system containing only beads without cells did not induce metHb/NO production.

As can be seen from Table 2 and FIG. 2, pravastatin appears to stimulate cNOS in much the same way as other NOS agonist described in U.S. Pat. No. 5,543,430 independent of its inhibitory effect on cholesterol biosynthesis.

Although the preferred methods have been described in detail, it should be understood that various changes, substitutions, and alterations can be made in the present invention as defined by the claims appended hereto. For example, other cNOS agonist may be identified. An example of a contemplated formulation is a mixture of estrogen and L-arginine since preliminary data indicates that estrogen may be functioning as a NOS agonist. The present invention is defined by the claims attached hereto.

What is claimed is:

1. A method of treating a disease condition in a subject by vasodilation or vasorelaxation comprising:

selecting a subject;

administering a mixture of L-arginine and an inhibitor of Hmg—CoA reductase wherein said inhibitor of Hmg—CoA reductase is selected from the group consisting of:

lovastatin;

pravastatin;

simvastatin;

fluvastatin;

dalvastatin;

compactin;

HR-780;

BMY 22,089;

BMY 22,566;

SQ 33,600;

GR 95,030; or

CI 981;

obtaining periodic indicators of vasorelaxations for the subject; and continuing administration of the mixture until a desirable state of vasorelaxation is obtained.

2. The method of claim 1, wherein the formulation is administered intravenously, buccal, intracoronary, intramuscularly, topically, intranasally, rectally, sublingually, orally, subcutaneously, by patch, or inhalation.

3. The method of claim 1, wherein said disease is hypertension, hypertensive heart disease, coronary heart disease, cardiovascular disease, cerebrovascular disease, and renovascular disease.

4. The method of claim 3, wherein said coronary heart disease is restenosis post angioplasty.

5. The method of claim 1, wherein L-arginine and said inhibitor of Hmg—CoA reductase are mixed in vivo.

6. The method of claim 5, wherein L-arginine and said inhibitor of Hmg—CoA reductase are administered at a therapeutic concentration.

7. The method of claim 6, wherein the therapeutic concentration of L-arginine is from 7.5% to about 30% w/v (g/ml).

8. The method of claim 6, wherein the therapeutic concentration of L-arginine is from 10% to about 15% w/v (g/ml).

9. The method of claim 6, wherein the therapeutic concentration of L-arginine is 10% w/v (g/ml).

10. The method of claim 6, wherein the pH is maintained within the range of 6 to 8.0.

11. The method of claim 6, wherein the pH is maintained within the range of 7 to 7.4.

12. The method of claim 1, wherein said inhibitor of Hmg—CoA reductase is pravastatin.

13. A therapeutic mixture comprised of an inhibitor of Hmg—CoA reductase and a substrate of NOS, said substrate of NOS being a biological equivalent of arginine, said inhibitor being selected from the group consisting of:

lovastatin;
pravastatin;
simvastatin;
fluvastatin;
dalvastatin;
compactin;
HR-780;
BMY 22,089;
BMY 22,566;
SQ 33,600;
GR 95,030; or
CI 981.

14. The therapeutic mixture of claim 13, wherein said inhibitor of Hmg—CoA reductase is an agonist of NOS.

15. The therapeutic mixture of claim 13, wherein said inhibitor of Hmg—CoA reductase is pravastatin.

16. The therapeutic mixture of claim 13, wherein said inhibitor of Hmg—CoA reductase is pravastatin and said biological equivalent of arginine is L-arginine.

17. A method of stimulating nitric oxide synthase to produce nitric oxide, said method comprising:

administering L-arginine and an agonist of nitric oxide synthase to a subject have a nitric oxide synthase receptor site, said agonist being different than L-arginine and being selected from the group consisting of:

lovastatin;
pravastatin;
simvastatin;
fluvastatin;
dalvastatin;
compactin;
HR-780;
BMY 22,089;
BMY 22,566;
SQ 33,600;
GR 95,030; or
CI 981 stimulating said nitric oxide synthase to a desirable level with said agonist of nitric oxide synthase.

18. The method of claim 17, wherein said L-arginine is in excess to said agonist.

19. The method of claim 17, wherein therapeutically effective amounts of L-arginine is combined with therapeutically effective amounts of said agonist prior to administering to the patient.

* * * * *